United States Patent [19]

Ferrin et al.

[11] Patent Number: 5,707,811
[45] Date of Patent: Jan. 13, 1998

[54] RECA-ASSISTED CLONING OF DNA

[75] Inventors: Lance Joseph Ferrin, Gaithersburg; R. Daniel Camerini-Otero, Kensington, both of Md.

[73] Assignee: The United States of America as represented by the Secretary of Health and Human Services, Washington, D.C.

[21] Appl. No.: 682,305

[22] Filed: Jul. 17, 1996

Related U.S. Application Data

[60] Provisional application No. 60/001,384 Jul. 21, 1995.
[51] Int. Cl.$^6$ ........................................................ C12Q 1/68
[52] U.S. Cl. ........................ 435/6; 935/23; 935/27; 435/91.1
[58] Field of Search ........................... 435/5, 6, 91.1, 435/91.4, 172.1, 172.3; 935/23, 27

[56] References Cited

U.S. PATENT DOCUMENTS 5,510,473   4/1996   Camerini-Otero et al. .......... 530/23.5

FOREIGN PATENT DOCUMENTS 0718404     6/1996   European Pat. Off. ........ C12N 15/63
WO 92/08791 5/1992   WIPO ........................... C12N 15/00

OTHER PUBLICATIONS

Barnes, W. (1994) PCR amplification of up to 35-kb DNA with high fidelity and high yield from λ bacteriophage templates. Proc. Natl. Acad. Sci. 91:2216–2220.

Barton, M., et al. (1994) Regulated expression of the β-globin gene locus in synthetic nuclei. Genes & Development 8:2453–2465.

Berger, S. (1994) Expanding the potential of restriction endonucleases: Use of hapaxoterministic enzymes. Analytical Biochemistry 222:1–8.

Brooks, S., et al. (1989) Sequence organization of the human int–2 gene and its expression in teratocarcinoma cells. Oncogene 4:429–436.

Camerini–Otero, R., et al. (1993) Parallel DNA triplexes, homologous recombination, and other homology–dependent DNA interactions. Cell 73:217–223.

Casey, G., et al. (1986) Characterization and chromosome assignment of the human homolog on int-2, a potential proto–oncogene. Molecular and Cellular Biology 6(2):502–510.

Cheng, S., et al. (1994) Effective amplification of long targets from cloned inserts and human genomic DNA. Proc. Natl Acad. Sci. 91:5695–5699.

Drake, J. (1991) A constant rate of spontaneous mutation in DNA–based microbes. Proc. Natl. Acad. Sci. 88:7160–7164.

Drmanac, R., et al. (1993) DNA sequence dtermination by hybridization: a strategy for efficient large–scale sequencing. Science 260:1649–1652.

Ferrin, L., et al. (1994) Long–range mapping of gaps and telomeres with RecA–assisted restriction endonuclease (RARE) cleavage. Nature Genetics 6:379–383.

(List continued on next page.)

*Primary Examiner*—W. Gary Jones
*Assistant Examiner*—Amy Atzel
*Attorney, Agent, or Firm*—Knobbe, Martens, Olson & Bear, LLP

[57] ABSTRACT

DNA is cloned and labeled in a sequence-specific manner. The DNA is digested with one or more restriction enzymes which produce 3' recessed ends. A desired fragment is protected from elongation by DNA polymerase by addition of E. coli RecA protein and oligonucleotides about 30 to 60 bases in length complementary to the 3' recessed ends of the digested fragment. RecA and DNA polymerase are then inactivated, leaving only the desired fragment with 3' recessed ends which is then ligated into a vector containing complementary 3' recessed ends.

26 Claims, 3 Drawing Sheets

OTHER PUBLICATIONS

Ferrin, L. (1995) Manipulating and mapping DNA with recA–assisted restriction endonuclease (RARE) cleavage. Genetic Engineering 17:21–30.

Ferrin, L., et al. (1991) Selective cleavage of human DNA: recA–assisted restriction endonuclease (RARE) cleavage. Science 254:1494–1497.

Foord, O., et al. (1994) Long–distance PCR. PCR Methods and Applications 3:S149–S161.

Gourdon, G., et al. (1994) Analysis of a 70 kb segment of DNA containing the human ζ and α–globin genes linked to their regulatory element (HS–40) in transgenic mice. Nucleic Acids Research 22(20):4139–4147.

Heineman, T., et al. (1994) Deletion of the varicella–zoster virus large subunit of ribonucleotide reductase impairs growth of virus in vitro. Journal of Virology 68(5):3317–3323.

Honigberg, S., et al. (1986) Ability of RecA protein to promote a search for rare sequences in duplex DNA. Proc. Natl. Acad. Sci. 83:9586–9590.

Jayasena, V., et al. (1993) Complement–stabilized D–loop RecA–catalyzed stable pairing of linear DNA molecules at internal sites. J. Mol. Biol. 230;1015–1024.

Jones, D., et al. (1991) A rapid method for recombination and site-specific mutagenesis by placing homologous ends on DNA using polymerase chain reaction. Biotechniques 10(1):62–66.

Kim, M., et al. (1995) Probing the structure of a putative intermediate in homologous recombination: the third strand in the parallel DNA triplex is in contact with the major . . . J. Mol. Biol. 247:874–889.

Labarca, C., et al. (1980) A simple, rapid, and sensitive DNA assay procedure. Analytical Biochemistry 102:344–352.

Pun, K., et al. (1990) Extraction of nucleic acids from agarose gel–a quantitative and qualitative comparison of four difference methods. Preparative Biochemistry 20(2):123–135.

Rigas, B., et al. (1986) Rapid plasmid library screening using RecA–coated biotinylated probes. Proc. Natl. Acad. Sci. 83:9591–9595.

Schaaper, R. (1993) Base selection, proofreading, and mismatch repair during DNA replication in *Escherichia coli*. The Journal of Biological Chemistry 268(32):23762–23765.

Sena, E., et al. (1993) Targeting in linear DNA duplexes with two complementary probe strands for hybrid stability. Nature Genetics 3:365–371.

Shinohara, A., et al. (1992) Rad51 protein involved in repair and recombination in S. cerevisiae is a RecA–like protein. Cell 69:457–470.

Taidi–Laskowski B., et al. (1988) Use of RecA protein to enrich for homologous genes in a genomic library. Nucleic Acids Research 16(16):8157–8169.

Taidi–Laskowski et al. (1988) *Nucleic Acids Research* 16:8157–8169.

Gnirke et al. (1994) *Genomics* 24:199–210.

Weiner et al. (1993) *Gene* 126:35–41.

Wetmur et al. (1994) *J. Biol. Chem.* 269:25928–35.

Koob et al. (1992) *Nucleic Acids Research* 20:5831–36.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 39 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

GATTATAGCT TTTCTAATTT AACCTTTGTC AGGTTACCA               39

(2) INFORMATION FOR SEQ ID NO:2:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:2:

GATTATAGCT TTGTGTGCCA CCCACTACGA CCTGCATAA               39

(2) INFORMATION FOR SEQ ID NO:3:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

AGCCTACGAT CGATGCCTTG ACAT                              24

(2) INFORMATION FOR SEQ ID NO:4:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

ATGCTAGCTA CGGAACTGTA GGAG                              24

(2) INFORMATION FOR SEQ ID NO:5:

(i) SEQUENCE CHARACTERISTICS:
    (A) LENGTH: 58 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GGTCCGAGTG CGCGGAATTC GTCTCACTAA GACACTCCGG TTCTCTCCAA AGCCAGGC   58

(2) INFORMATION FOR SEQ ID NO:6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

TGGTCCTAGC TTGGATCCCA TGTACCCTTG GCAAAGCATT CTACTGCCCA CATCCCC   57

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

AATTCTACCA GAGGTACAAG GAGGA   25

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

GATGGTCTCC ATGTTCCTCC TA   22

(2) INFORMATION FOR SEQ ID NO:9:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

```
-continued
TGAAAATATT GAACAGTGAA TAAAGCATAA AAAAAAAATG TCGGATCCAT AGCGCTAT                58
```

( 2 ) INFORMATION FOR SEQ ID NO:10:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

```
GGACTTACCT GTCCTGAATT CACCGAAAAG CTCAGTAATA GAACCAGTTT CCACACC                 57
```

RECA-ASSISTED CLONING OF DNA

RELATED APPLICATION

This application claims the benefit of priority under 35 U.S.C. §119(e) of provisional application No. 60/001,384, filed Jul. 21, 1995.

1. Field of the Invention

The present invention relates to the sequence-specific cloning and labeling of DNA using the RecA protein. More specifically, the invention relates to the ability of RecA to selectively pair oligonucleotides to their homologous sequences at the 3' recessed ends of digested duplex DNA fragments and to protect these 3' ends from enzymatic conversion to blunt ends, thus facilitating cloning of a desired DNA fragment.

2. Background of the Invention

The isolation and cloning of genomic DNA fragments is of paramount importance to the biomedical sciences. In this regard, several methods are available to amplify DNA and to isolate selected fragments in pure form. The most widely used amplification method is the polymerase chain reaction (PCR). In this method, oligonucleotide primers flanking a desired DNA sequence are used to amplify the sequence by repeated rounds of denaturation, annealing and extension steps. However, a major limitation of PCR is the small fragment size which may be reliably amplified, although recent improvements have allowed amplification of up to 22 kilobases (kb) (Cheng et al., *Proc. Natl. Acad. Sci. U.S.A.*, 91:5695, 1994; Foord et al., *PCR Methods and Applications*, 3:S149, 1994).

Other widely used methods of cloning genomic DNA fragments involve the construction and screening of DNA libraries, most commonly λ phage and cosmid vectors. Other vectors are now gaining widespread use for cloning large (>100 kb) segments of DNA including yeast artificial chromosomes (YACs), bacterial artificial chromosomes (BACs) and P1 phage derived artificial chromosomes (PACs). Such libraries, however, are difficult to construct and screen.

*E. coli* RecA protein has been used to screen libraries and to enrich for a selected DNA fragment (Rigas et al., *Proc. Natl. Acad. Sci. U.S.A.*, 83:9591, 1986; Honigberg et al., *Proc. Natl. Acad. Sci. U.S.A.*, 83:9586, 1986; Taidi-Laskowski et al., *Nucl. Acids. Res.*, 16:8157, 1988; Sena et al., *Nature Genet.*, 3:365, 1993; Jayasena et al., *J. Mol. Biol.*, 230:1015, 1993). These methods are based on the ability of RecA to specifically target single-stranded DNA to complementary target duplex DNA to create a three-stranded complex (Camerini-Otero et al., *Cell*, 73:217, 1993), or to pair two complementary single strands to the target duplex DNA to create a four-stranded complex. These strategies have not been applied to practical problems in molecular biology.

RecA-Assisted Restriction Endonuclease (RARE) Cleavage is a general and efficient method of targeting restriction enzyme cleavage to unique predetermined sites and is described in U.S. patent application Ser. No. 08/089,910, the entire contents of which are hereby incorporated by reference, and by Ferrin et al. (*Nature Genet.*, 6:379, 1994). This method is based on the ability of RecA to pair oligonucleotides to homologous sequences in duplex DNA to form three-stranded complexes. These complexes protected the selected sites from enzymatic manipulation, and, after removal of the complexes, restriction enzyme cleavage was limited to the selected unmethylated sites. This method has been used to map and manipulate large segments of DNA (Ferrin, in *Genetic Engineering: Principles and Methods*, J. Setlow, Ed., Plenum Press, New York, 17:21–30, 1995; Barton et al., *Genes and Dev.*, 8:2453, 1994; Heineman et al., *J. Virol.*, 68:3317, 1994; Gourdon et al., *Nucl. Acids. Res.*, 22:4139, 1994).

Because of the practical size limitations of PCR cloning and the labor-intensive steps required in genomic DNA library construction and screening, there is a need for a simple, efficient method of labeling and cloning large fragments of genomic DNA. The present invention addresses this need.

SUMMARY OF THE INVENTION

One aspect of the present invention is a method of cloning a genomic DNA fragment containing a predetermined DNA sequence. The method includes digesting DNA containing a predetermined DNA sequence with at least one restriction enzyme which generates 3' recessed ends to produce DNA fragments having 3' recessed ends. The DNA fragments are reacted with RecA protein and two oligonucleotides. These oligonucleotides are complementary to either DNA strand of the fragment coning the predetermined DNA sequence. In a preferred embodiment, the oligonucleotides are 30 to 60 nucleotides in length. The resulting fragments are then reacted with a DNA polymerase. As a result, all DNA fragments except the fragment containing the predetermined DNA sequence become blunt-ended. The oligonucleotides are dissociated from the ends of the fragment containing the predetermined DNA sequence. The DNA fragments are then ligated to a vector having 3' recessed ends complementary to those produced by the restriction enzyme. Only the fragment containing the predetermined DNA sequence is incorporated into the vector. The vector can be a plasmid, such as pBC SK$^+$ or pBS SK$^+$. Advantageously, the vector is a yeast artificial chromosome, bacterial artificial chromosome or P1 phage artificial chromosome. Preferably, the restriction enzyme is EcoRI or a combination of EcoRI and BamHI. Advantageously, the DNA polymerase can be the exonuclease-deficient mutant of the Klenow fragment of *E. coli* DNA polymerase I.

The method can further comprise the step of size fractionating said DNA fragments of step (a) to enrich for the fragment containing the predetermined DNA sequence. This embodiment can further comprise, prior to the ligating step, ligating the enriched DNA fragments to a biotinylated duplex containing complementary 3' recessed ends, wherein the biotinylated duplex is bound to streptavidin-coated beads. In addition, the method can further comprise amplifying the DNA fragment containing the predetermined DNA sequence. Preferably, the amplifying step comprises transfection into bacteria or PCR.

The present invention also provides a method of diagnosing a genetic mutation in a mammal in which a variation of the above method is used. In this method, the fragment containing the fragment is amplified and it is determined if the mutation is present. Amplification can be by growth of the vector in a suitable microorganism or through PCR. Determination of the presence of the mutation can be accomplished by sequencing the fragment. Preferably, the mammal is a human and the DNA polymerase is the exonuclease-deficient mutant of the Klenow fragment of *E. coli* DNA polymerase I. The method can further comprise the step of size fractionating the DNA fragments of step (a) to enrich for the fragment containing the mutation. The method can also further comprise prior to the ligating step, ligating the enriched DNA fragments to a biotinylated duplex containing complementary 3' recessed ends, wherein the biotinylated duplex is bound to streptavidin-coated beads. In addition, the method can further comprise amplifying the DNA fragment containing the predetermined DNA sequence.

Another aspect of the present invention provides an article of manufacture which includes packaging material and at one or more reagents for cloning of DNA. The reagents for cloning of DNA includes recA, and the packaging material includes instructions for using the reagents to clone DNA, such as by the method described above. The reagents can also include one or more restriction enzymes capable of generating 3' recessed ends, DNA polymerase and a vector having 3' cohesive ends. The 3' cohesive ends are preferably complementary to the 3' recessed ends generated by the restriction enzymes. In one embodiment, these restriction enzymes are EcoRI and BamHI. The DNA polymerase can be the Klenow fragment of *E. coli* DNA polymerase I, and the vector can be a plasmid.

DETAILED DESCRIPTION OF THE PREFERRED EMBODIMENTS

Figure 1:
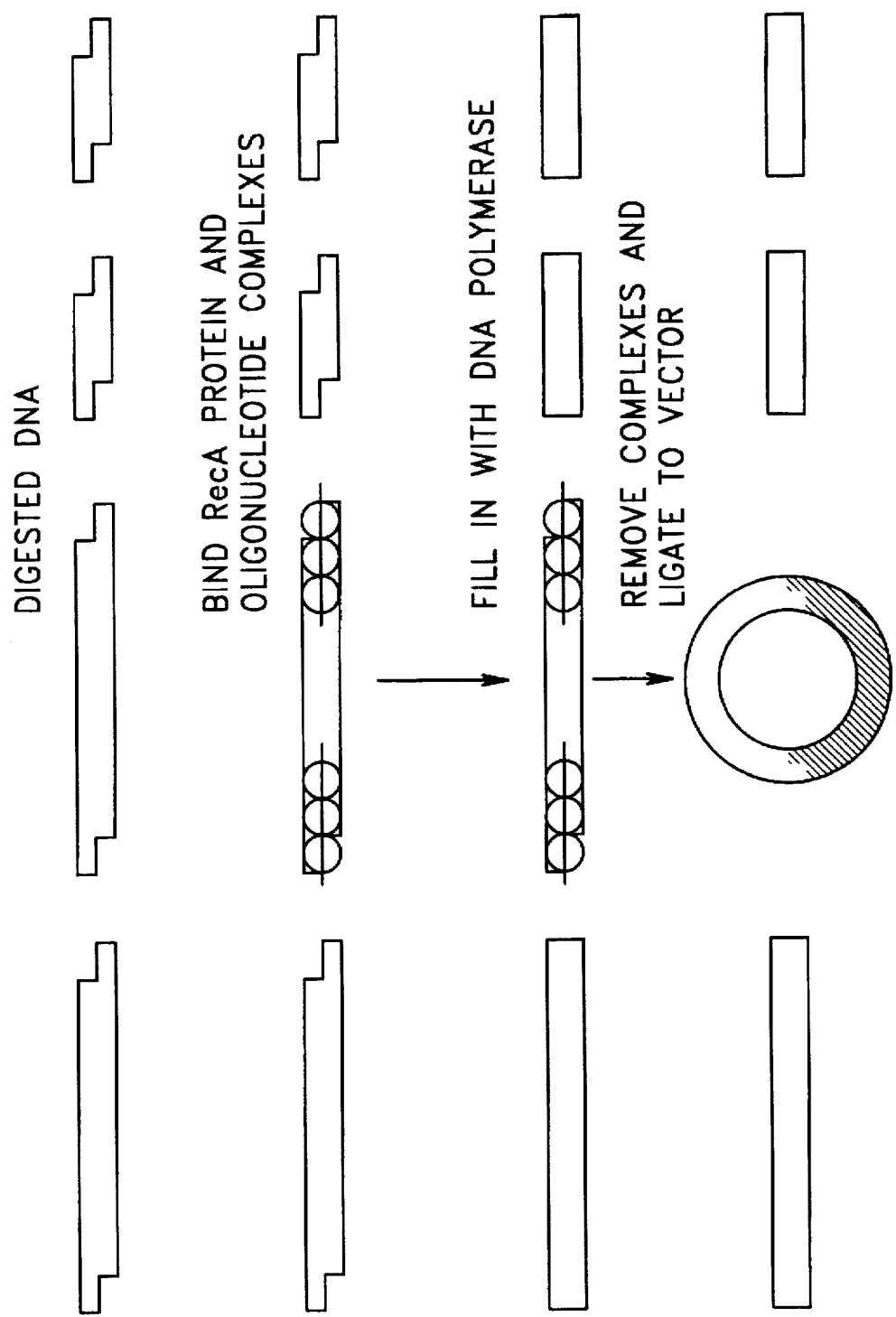
FIG. 1 is a schematic diagram of the strategy used for sequence-specific RecA-mediated amplification of DNA. The RecA-oligonucleotide complexes are indicated by the adjacent circles having a line passing through their centers.
Figure 2:
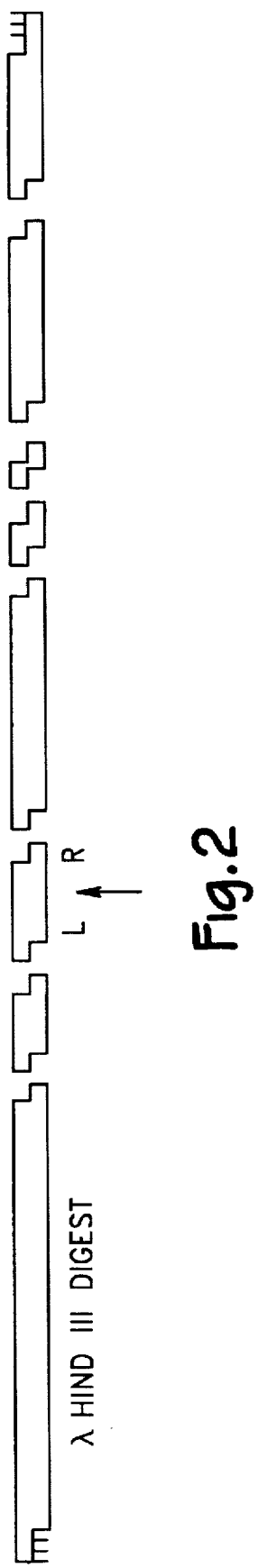
FIG. 2 is a schematic diagram of λ DNA digested with HindIII. The 2.3 kb fragment labeled by RecA-Assisted cloning is indicated by the arrow. The left (L) and right (R) 3' ends to which the L and R oligonucleotides are complementary are shown.

The present invention relates to a method of sequence-specific genomic DNA cloning. This method is based on the ability of *E. coli* RecA protein to selectively pair oligonucleotides to their complementary sequences at the ends of duplex DNA. Genomic DNA is digested with one or two restriction enzymes which produce 3' recessed ends (5' overhangs). After addition of RecA protein and a pair of oligonucleotides, each complementary to one of the ends of a genomic DNA fragment of interest, the resulting three-stranded complexes become resistant to elongation by DNA polymerase and thus retain their 3' recessed ends after addition of the enzyme, while the unprotected genomic DNA fragments are filled in by the polymerase, thus becoming blunt-ended. Because most restriction endonucleases produce fragments having 3' recessed ends, these fragments were targeted for amplification using the method of the present invention. By using ligation conditions and vectors which greatly favor ligation to 3' recessed ends, protected fragments are selectively cloned. The vector into which the genomic DNA fragment is to be inserted is digested with the same restriction enzyme(s) as was the genomic DNA, or with a restriction enzyme(s) that produce the same 5' overhangs, resulting in complementary 3' recessed ends for insertion of the genomic DNA fragment.

The oligonucleotides used in the present method are complementary to a portion of the ends of a desired DNA fragment, including the 5' overhangs themselves. For example, digestion with EcoRI produces the 5' overhang TTAA. Thus, the oligonucleotides are complementary to this sequence plus additional sequence of the genomic DNA fragment adjacent to the overhang which is complementary to the remainder of the oligonucleotide. It will be appreciated that an oligonucleotide complementary to one DNA strand is identical in sequence to the other DNA strand. Of course, the oligonucleotides can be complementary to either strand at the end of the DNA duplex. Further, the oligonucleotides can also include additional nonhomologous sequences at their 5' or 3' ends; although these "nonhomologous tails" do not ordinarily increase the efficiency of protection. In addition, it is contemplated that only a single end of a desired DNA fragment can be protected with an oligonucleotide complementary thereto. In fact, a 200-fold enrichment of a particular DNA sequence can be obtained by protection of one end of a DNA fragment. This entails cloning using a vector having one cohesive and one blunt end, or cutting the DNA fragment with another enzyme after the polymerase reaction.

The present invention has a number of important applications, including fast DNA cloning, DNA amplification in bacteria or by PCR, DNA sequence-based diagnostic tests and automated high-throughput DNA sequencing. The reagents for performing the method can also be supplied as a diagnostic kit for identification of mutations in a particular gene sequence. Genomic DNA can be digested with any single restriction enzyme which produces 3' recessed ends or any two different enzymes which produce 3' recessed ends. Such restriction enzymes are well known in the art and include, for example, BamHI, EcoRI, HindIII, HinfI, HpaII, MluI and XbaI. In the preferred embodiment, oligonucleotides 30 to 60 bases in length are used, each having complete complementarity to the ends of the desired DNA fragment. Shorter and longer oligonucleotides can also be used, although reduced efficiency can sometimes result. A DNA polymerase and the four deoxynucleoside triphosphates are then added and allowed to fill in all available single-stranded sites with the exception of the fragment protected by the RecA-oligonucleotide complexes. In a preferred embodiment, The exonuclease-free Klenow Fragment (KF) of *E. coli* DNA polymerase I is used. This enzyme is efficient at creating blunt ends, can be added in excess without degrading DNA, is blocked by RecA-oligonucleotide complexes and is easily inactivated after completion of the reaction. The use of other DNA polymerases in the present method is also contemplated.

The RecA and KF enzymes are then inactivated, causing the RecA/oligonucleotide complex to dissociate from the DNA duplex. This inactivation can be accomplished by, for example, treatment with sodium dodecyl sulfate or phenol/chloroform extraction. The vast majority of the resulting DNA fragments in the mixture contain blunt ends as a result of the action of KF. However, the DNA fragment containing the predetermined DNA sequence of interest retains its 3' recessed ends as a result of the protection afforded by the RecA/oligonucleotide complex. These fragments can then be easily ligated into a vector having complementary 3' recessed ends.

After enrichment for a particular fragment, the fragment is ligated to a vector containing the appropriate 3' recessed ends. The insert is then amplified by, for example, transforming bacteria with the insert-containing plasmid or by PCR. Because DNA fragments having complementary 3' recessed ends are ligated to the vector much more readily than DNA fragments containing blunt ends, the resulting clones are highly enriched for the selected fragment.

In a preferred embodiment, in the cloning of genomic DNA fragments, it is desirable to size fractionate the digested DNA prior to the RecA/KF protection reaction to augment the enrichment of a particular fragment and to eliminate the cloning of small fragments. This can be accomplished by, for example, using an agarose gel followed by recovery of DNA from the relevant molecular weight region of the gel. In another preferred embodiment, the size fractionated DNA is ligated to both a short biotinylated duplex bound to streptavidin-coated beads which terminates with the same cohesive end as that produced by digestion with the restriction enzyme(s) used to digest the genomic DNA, and to a vector which has been digested with a restriction enzyme which produces 3' recessed ends complementary to those produced after digestion of the genomic DNA. Alternatively, the ligation reaction can be performed in two steps. In a preferred embodiment, the vector is a plasmid. Other vectors are also contemplated including baeteriophage vectors such as λ; eukaryotic expression vectors such as the LacSwitch™ inducible mammalian expression system (Stratagene), adenoviral vectors and the like. Particularly preferred vectors for the propagation of large DNA fragments include YACs, BAGs and PACs. The vector is then used to transform cells which are expanded, resulting in amplification of the selected DNA fragment. Alternatively, the fragment can be amplified using PCR.

RecA-Assisted cloning has sufficient specificity to allow cloning directly from genomie DNA and is a much easier alternative than construction and screening of DNA libraries. The technique is preferable to PCR in the cloning of large (greater than about 5 kb) or highly repetitive fragments of DNA, especially if absolute fidelity is required due to the lower error rate of RecA-Assisted Cloning versus PCR.

RecA-Assisted Cloning can be used to identify specific mutations in a gene which give rise to genetic abnormalities and thus is useful in screening patients for genetic abnormalities or mutations which will predispose patients to certain conditions. Such mutations include point mutations, insertions and deletions. One particular use in this regard is in fetal screening. Fetal cells can be obtained by amniocentesis and analyzed for genetic defects including Tay-Sachs, sickle cell anemia, β-thalassemias, and any other desired genetic disease. Specific oligonucleotides are designed which will hybridize to the 3' ends of the fragment containing the DNA sequence of interest.

Many modifications of RecA-Assisted Cloning are contemplated. For example, the RecA/KF reactions worked well on DNA embedded in agarose which will be useful for molecities that would tend to shear in solution. For applications in which increased specificity is desired, RecA-Assisted Cloning can be used after RARE cleavage, or with type IIs restriction enzymes that create varied and asymmetric staggered ends unrelated to their recognition sites (Berger, *Anal. Blochem.*, 222:1, 1994). Increases in specificity would also be useful for labeling specific genomic DNA fragments using RecA-Assisted Cloning and is a viable alternative to detection methods such as Southern blotting. In addition, if conditions can be found that allow labeling of very short duplexes, the method can be a useful adjunct to sequencing by oligonueleotide array methods (Drmanac et al., *Science* 260:1649, 1993).

Sequence-specific labeling of a λ DNA fragment using RecA-Assisted Cloning was performed as described below.

EXAMPLE 1

Sequence-specific Labeling of a 2.3 kb λ DNA Fragment

*E. coli* RecA protein was prepared as described (Ferrin et al., *Science*, 254:1494, 1991) using an overproducing strain provided by Barbara McGrath of the Brookhaven National Laboratory, or purchased from Boehringer Mannheim (Indianapolis, Ind.). The sequence of the L oligonucleotide was 5'-gattatAGCTTTTCTAATTTAACCTTTGTCA-GGTTACCA-3' (SEQ ID NO:1), and the R oligonucleotide was 5'-gattatAGCTTTGTGTGCCACCCACTACGA-CCTGCATAA-3' (SEQ ID NO:2).

The lower case letters indicate sequences of nonhomologous tails, and the capital letters indicate the sequences of portions homologous to the ends of the λ fragment. Oligonucleotides over 30 bases in length were purified on acrylamide gels and concentrations were measured as described (Ferrin et al., supra).

The RecA protection reaction volume was 100 µl and contained 25 mM Tris-acetate, pH 7.85, 4 mM magnesium acetate, 0.4 mM dithiothreitol, 0.5 mM spermidine, 1.1 mM ADP, 0.3 mM ATP-γ-S (Fluka), 13 µg of RecA protein, 0.32 L or R oligonucleotide (or 0.16 µg each of L and R), 2.5 µg of HindIII-digested λ DNA (New England Biolabs, Beverly, Mass.) and 40 µg bovine serum albumin (BSA; Sigma, St. Louis, Mo.), 38 µM each of dATP, dCTP, dGTP and TTP, and 12.5 units of KF (United States Biochemical, Cleveland, Ohio). After a 10 minute incubation at 37° C., KF and deoxynucleoside triphosphates were added and the reaction allowed to proceed for 30 minutes at 37° C. RecA and KF were then inactivated by extraction with phenol/chloroform (1:1), followed by extraction three times with diethyl ether, addition of sodium acetate to 0.3M and precipitation with ethanol. The pellets were washed with 70% ethanol followed by ligation to the following short radioactive duplex for one hour at room temperature:

5'-AGCTTACGATCGATGCCTTGACAT-3' (SEQ ID NO:3)

3'-ATGCTAGCTACGGAACTGTAGGAG-5' (SEQ ID NO:4)

The HindIII cohesive end is at the left, and the bottom strand was labeled with γ-$^{32}$P-ATP using polynucleotide kinase. The kinase was heat-inaetivated at 65° C. for 10 minutes and the unreacted γ-$^{32}$P-ATP was removed by gel filtration (Chroma Spin+TE-10 columns; Clontech, Palo Alto, Calif.) prior to adding the top strand. The ligation reaction had a volume of 40 µl and contained 1.0 µg λ DNA, 0.8 µg labeled duplex, 8 units of *E. coli* DNA ligase, and the buffer recommended by New England Biolabs without BSA. Excess duplex was removed by gel filtration followed by addition of bromphenol blue and glycerol. The samples were heated to 65° C. for 3 minutes and analyzed by agarose gel electrophoresis. Quantitation was performed using a Fuji Phosphor Imager and yields were calculated by comparison to the 2.3 kb band obtained from the reaction mixture containing the L oligonucleotide, but lacking KF after a small correction for a portion of the band removed by ligation to other fragments.

Efficient labeling of only the 2.3 kb band occurred when the HindIII-digested λ DNA was incubated with the L oligonueleotide, the R oligonucleotide and KF. In this case, the L and R oligonucleotides were used to protect both the left and the right ends of the 2.3 kb λ DNA fragment followed by ligation of the short labeled duplex to both ends. When only the L or R oligonucleotide was used, each band on the agarose gel was only about half the intensity of the band obtained using both oligonucleotides. No specific labeling was observed if the ends were not protected (neither L nor R present), or when the restriction enzyme used to fragment the starting λ DNA produced blunt ends. In addition, all of the fragments were labeled when KF was omitted.

The protection efficiency at each end of the 2.3 kb fragment was about 90%. Nonspecific protection of other ends was detectable, but less than 0.5%, and labeling of the DNA with blunt ends was undetectable. Only 29 bases of sequence information at each end of the duplex was used in designing the oligonucleotides (33 bases if the 4 base single-stranded tail produced by HindIII is counted). A series of nine oligonucleotides was synthesized using an automated DNA synthesizer to investigate the parameters that determine protection efficiency. The efficiency was the same when the oligonucleotide contained 41 homologous bases, but dropped to 76% with 19 bases, and to less than 1% with 10 bases.

The oligonucleotides could have the same sequence at either strand at the end of the duplex without changing the efficiency. Addition of a tail that extended the oligonucleotide past the end of the fragment did not change the efficiency. These results were slightly more favorable than with RARE cleavage, and probably reflected the increased stability of complexes formed at the end of duplexes (Kim et al., *J. Mol. Biol.*, 247:874, 1995).

To demonstrate RecA-assisted cloning using genomic DNA, we cloned a 1.4 kb EcoRI-BamHI fragment of the human int-2 proto-oncogene as described in the following example.

EXAMPLE 2

RecA-assisted Cloning of Genomic DNA

The human int-2 proto-oncogene has been mapped and sequenced (Casey et al., *Mol. Cell. Biol.*, 6:502, 1986; Brookes et al., *Oncogene*, 4:429, 1989). In this gone, one EcoRI site lies just upstream of oxon 2 and, in about half of the alleles, a BamHI site is 6.9 kb downstream of the EcoRI site. Human genomic DNA was isolated from multiple placentas (Sigma), digested with EcoRI and BamHI, extracted with phenol/chloroform and ethanol precipitated as described in Example 1. Yields after the ethanol precipitation were typically about 60%. Digested DNA was size fractionated on a 0.8% SeaPlaque GTG (FMC BioProducts) agarose gel in TAE buffer (Sambrook et al., *Molecular Cloning: a Laboratory Manual*, Cold Spring Harbor Laboratory Press, Plainview, N.Y., Second Edition, 1989). Multiple wells were loaded with 150–200 µg DNA per well. The gels were run until the 1.4 kb fragment had migrated 4 to 6 cm. The marker lane was then removed, stained with ethidium bromide and used as a guide to excise 0.5 cm above and below the position of the 1.4 kb fragment. Size fractionalion resulted in a modest sequence enrichment (about ten fold); a ten-fold decrease in the amount of reagents required; and eliminated small fragments that would preferentially be represented in the final clones.

DNA was extracted from the excised gel using GELase® (Epicentre) according to the manufacturer's directions; complete digestion was required for good yields. The yield of the complete protocol was 2 to 4%. Comparable yields were obtained with a silica gel extraction kit (Qiagen) or by electroelution (Pun et al., *Prep. Biochem.*, 20:123, 1990). The size of the extracted DNA from the heavily overloaded gels was checked on analytical gels. Depending on the amount available, DNA was quantified by absorbance, fluorescence (Labarea et al., *Anal. Biochem.*, 102:344, 1980), or spotting in an ethidium bromide solution (Sambrook et al., 1989).

The size-fractionated doubly digested human placental DNA was used as the starting DNA for the RecA protein/KF protection reaction. The conditions for this reaction were the same as described in Example 1 with the exception that the total volume was 1440 µl and contained 3.2 µg of each oligonucleotide, 360 µg RecA protein, 2.6 µg fractionated DNA, 570 µg BSA and 450 units of KF. One nucleotide was identical to the int-2 genomic sequence from 2290–2347:

5'-GGTCCGAGTGCGCGGAATTCGTCTCAC-
TAAGACACTCCGGTTCTCTCCAAAGCC-
AGGC-3'      (SEQ ID NO:5), and the other was complementary to 3621–3677:

5'-TGGTCCTAGCTTGGATCCCATGTACCCT-
TGGCAAAGCATTCTACTGCCCACAT-
CCCC-3'      (SEQ ID NO:6).

EcoRI and BarnHi cleave 3' of residues 2304 and 3660, respectively (Casey et al., 1986; Brookes et al., 1989).

The protected fragments were ligated both to the pBS SK⁺ vector (Stratagene, La Jolla, Calif.) and to DNA bound to streptavidin beads using T4 DNA ligase. This step reduces the number of clones containing only vector DNA. When plasmid or λ vectors were simply ligated to DNA from the RecA protein/KF reaction, the vast majority of clones did not contain an insert. Efforts were made to reduce this background by decreasing the vector concentration, but this also lowered the efficiency of the cloning procedure. Due to the low mount of the selected fragment in genomic DNA, a large concentration of vector facilitated the intermolecular vector-fragment ligation.

Figure 3:
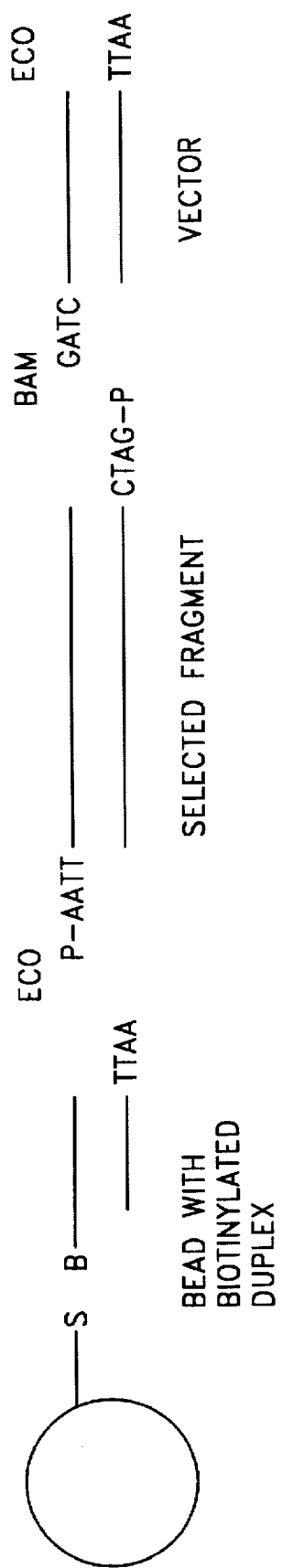
FIG. 3 is a schematic diagram of the construct resulting from ligation of the 1.4 kb human int-2 genomic DNA fragment to a vector and to a biotinylated DNA duplex bound to a streptavidin-coated bead. EcoRI and BamHI restriction sites and 4 base pair 5' overhangs are shown. S, streptavidin; B, biotin; and P, 5' phosphate.

Ligation of the 1.4 kb fragment to the vector and to the biotinylated DNA duplex bound to the streptavidin-coated beads is schematically shown in FIG. 3. Magnetic streptavidin beads (2 mg; Dynabeads M-280, Dynal) were used according to the manufacturer's instructions and saturated with the following duplex that contained an EcoRI cohesive end that lacked a 5' phosphate:

5'-AATTCTACCAGAGGTACAAGGAGGA-3' (SEQ ID NO:7)

3'-GATGGTCTCCATGTTCCTCCTA-5' (SEQ ID NO:8)

The oligonucleotide shown in SEQ ID NO:8 was synthesized with a biotin group at the 5' end using the LC Biotin-ON phosphormidite (Clontech). After binding, excess duplex was removed by washing the beads with 1M NaCl, 50 mM Tris-HCl, pH 7.5, followed by T4 DNA ligase buffer (New England Biolabs). Vector was prepared by treating pBS SK⁺ with EcoRI, BamHI and calf intestinal phosphatase. The small polylinker fragment arising from the digestion was removed by gel filtration. The ligation reaction contained the washed beads and 80 µl of T4 DNA ligase buffer with 20% of the DNA from the RecA protein/KF protection reaction, 0.34 µg of vector and 3,200 units of T4 DNA ligase. After 16 hours at 16° C., unligated DNA and vector were removed by washing the beads. The oligonucleotide shown in SEQ ID NO:7 (0.3 µg) was added to replace any removed by washing. The BamHI site on the other side of the fragment was available to ligate to the vector.

Immobilized fragment-vector DNA was removed by treatment with 80 units of EcoRI in 100 µl EcoRI buffer. The solution containing the fragment-vector DNA was removed from the beads, extracted and ethanol precipitated as described in Example 1, except that 20 μg glycogen was added before the ethanol. To circularize the fragment-vector molecules, the DNA was treated with 1,600 units of T4 DNA ligase in 100 μl of T4 ligase buffer for 16 hours at 16° C. The DNA was concentrated by ethanol precipitation and used to transform 50 μl of *E. coli* XL-1 Blue MRF' (Stratagene) by electropotation in 0.1 cm cuvettes and a Gene Pulser apparatus (Bio-Rad, Richmond, Calif.). The cells were prepared for electroporation according to the instructions provided by Bio-Rad and yielded $8 \times 10^8$ colonies per μg of plasmid DNA using standard 0.2 cm cuvettes. Cells were plated on Luria Broth (LB) agar containing ampicillin, tetracycline, isopropylthio-β-D-galactoside (IPTG) and X-gal (Sambrook et al., 1989). Plasmid DNA was obtained by scraping and washing the resulting 7,000 white and 900 blue colonies from the plates with LB. Plasmid DNA was prepared using a kit (Qiagen) and extracted with cetyltrimethylammonium bromide (Ausubel, F., Ed., *Current Protocols in Molecular Biology*, Wiley, New York, 1995) to remove enzyme inhibitors.

Both the starting human placental DNA and the DNA obtained by RecA-Assisted Cloning were digested with EcoRI and BamHI and analyzed by agarose gel electrophoresis and Southern blotting. After staining with ethidium bromide, a large smear was observed in the lane containing digested human placental DNA, while only vector DNA was visible in the lane containing the DNA obtained by RecA-Assisted Cloning, although a faint smear of insert DNA centered at around 1.4 kb was observed on another gel containing twice as much DNA. The agarose gel was blotted onto charged nylon membranes using standard techniques, and the nylon membrane was probed with a labeled fragment (SS6) containing 0.6 kb of the selected int-2 fragment (Casey et al., 1986; Brookes et al., 1989).

The amount of the int-2 fragment was 20 times greater in the lane containing the RecA-cloned DNA as compared to the lane containing digested genomic DNA, even though the genomic DNA lane contained 80 times more DNA than the cloned DNA lane. Thus, a 1600-fold enrichment of the fragment was obtained by RecA-Assisted Cloning. These results reflected cloning of a fragment present at only about one copy per diploid human genome.

EXAMPLE 3

Multiple Cloning Trials

Multiple cloning trials were performed using both yeast and human DNA. With human DNA, the typical enrichment was 1,000 to 2,000-fold, and one int-2 clone was present for every 2,000 to 4,000 colonies. At least one int-2 clone was obtained for every 70 μg of starting genomic DNA. When the pooled DNA after one round of RecA-Assisted Cloning was subjected to the procedure a second time, 24% of the colonies contained the int-2 fragment. The procedure was essentially identical to that described in Example 2, except that the RecA/KF reaction step was scaled down by a factor of 14. pBC SK+ was used as the vector and clones were selected on chloramphenicol plates to eliminate any background from the previous plasmid vector which contained an ampicillin resistance gene. This demonstrated an additional 500-fold enrichment and showed that incorrect clones arose mainly through a stochastic process, and not through a biased selection based on partial homology to the int-2 sequence. A 1.2 kb EcoRI-BamHI yeast genomic DNA fragment containing the proximal portion of the RAD51 gene (Shmohara et al., *Cell* 69:457, 1992) was also cloned. The oligonucleotides used to clone this fragment had sequences complementary to positions 1–48:

5'-TGAAAATATTGAACAGTGAATAAAGCAT-
AAAAAAAAAATGTCGGATCCATA-
GCGCTAT-3'        (SEQ ID NO:9), and 1164–1204:

5'-GGACTTACCTGTCCTGTCCTGAATTCAC-
CGAAAAGCTCAGTAATAGAACCAG-
TTTCCACACC-3'        (SEQ ID NO:10).

The yeast genomic DNA was isolated as described by Ausubel (ibid. (p.13)). Conditions were identical to those described in Example 2, except that the RecA/KF reaction was scaled down by a factor of 14. pBC SK+ was used as the vector and clones were selected on chloramphenicol plates.

Plasmid DNA from 10 int-2 clones and 10 RAD51 clones were analyzed by restriction enzyme mapping. No rearrangements were detected. The sequences of the two vector-insert junctions and about 400 bases of insert DNA of each of the 20 clones were determined. Plasmid DNA was prepared using a kit (Qiagen). Digestions were performed with EcoRI and BamHI and analyzed by electrophoresis on an agarose gel. Sequencing was performed on an Applied Biosystems model 373 sequencer using their PRISM DyeDeoxy Terminator Cycle Sequencing kit and the M13-20 and reverse primers. No clear deviations from the published sequences were detected, but as ambiguities in the sequences occurred at a rate of about 1%, this could only be used to set an upper limit to the error rate of RecA-Assisted Cloning. One might expect the error rate to be closer to the in vivo error rate in *E. coli* of $10^{-10}$ mutations/bp/chromosome duplication (Schaaper et al., *J. Biol. Chem.*, 268:23762, 1993; Drake, *Proc. Natl. Acad Sci. U.S.A.*, 88:7160, 1991). rather than the PCR error rate of about $10^{-5}$ (Barnes, *Proc. Natl. Acad Sci. U.S.A.*, 91:2216, 1994).

Although the invention has been described with reference to particular preferred embodiments, the scope of the invention is defined by the appended claims and should be construed to include reasonable equivalents.

---

What is claimed is:

1. A method of cloning a DNA fragment containing a predetermined DNA sequence, comprising the steps of:
   (a) digesting DNA coning a predetermined DNA sequence with at least one restriction enzyme which generates 3' recessed ends to produce DNA fragments having 3' recessed ends;
   (b) reacting said DNA fragments with RecA protein and two oligonucleotides, said oligonucleotides being complementary to the 3' recessed end of either DNA strand of the fragment containing the predetermined DNA sequence;
   (c) reacting the DNA fragments resulting from step (b) with a DNA polymerase, whereby all DNA fragments except the fragment coming the predetermined DNA sequence become blunt-ended;
   (d) dissociating said oligonucleotides from the ends of the fragment containing the predetermined DNA sequence; and
   (e) ligating said DNA fragments to a vector having 3' recessed ends complementary to those produced by the restfiction enzyme, whereby only the fragment containing the predetermined DNA sequence is incorporated into said vector.

2. The method of claim 1, wherein said oligonucleotides are between 30 and 60 bases in length.

3. The method of claim 1, wherein said restriction enzyme is EcoRI.

4. The method of claim 1, wherein two restriction enzymes are reacted in step (a).

5. The method of claim 4, wherein said restriction enzymes are EcoRI and BamHI.

6. The method of claim 1, wherein said DNA polymerase is the Klenow fragment of E. coli DNA polymerase I.

7. The method of claim 1, wherein said vector is a plasmid.

8. The method of claim 7, wherein said plasmid is pBC SK+ or pBS SK+.

9. The method of claim 1, wherein said vector is a yeast artificial chromosome, bacterial artificial chromosome or P1 phage derived artificial chromosome.

10. The method of claim 1, further comprising the step of size fractionating said DNA fragments of step (a) to enrich for the fragment containing the predetermined DNA sequence.

11. The method of claim 10, further comprising, prior to the ligating step, ligating the enriched DNA fragments to a biotinylated duplex containing complementary 3' recessed ends, wherein said biotinylated duplex is bound to streptavidin-coated beads.

12. The method of claim 1, further comprising amplifying the DNA fragment containing the predetermined DNA sequence.

13. The method of claim 12, wherein said amplifying step comprises transfection into bacteria.

14. The method of claim 12, wherein said amplifying step comprises PCR.

15. A method of determining a genetic mutation in a mammal, comprising the steps of:
   (a) isolating genomic DNA containing said mutation from a mammal;
   (b) digesting said genomic DNA with one or more restriction enzymes which generate 3' recessed ends to produce genomic DNA fragments having 3' recessed ends;
   (c) reacting said genomic DNA fragments with RecA protein and two oligonucleotides, said oligonucleotides being complementary to the ends of the fragment containing the mutation;
   (c) reacting the genomic DNA fragments resulting from step (b) with a DNA polymerase, whereby all genomic DNA fragments except the fragment containing the mutation become blunt-ended;
   (d) dissociating said oligonucleotides from the ends of the fragment containing the mutation;
   (e) ligating said DNA fragments to a vector having 3' recessed ends complementary to those produced by the restriction enzyme(s), whereby only the fragment containing the mutation is incorporated into said vector;
   (f) amplifying the fragment containing the mutation; and
   (g) determining whether the mutation is present in the amplified fragments.

16. The method of claim 15, wherein step (f) comprises growth of said vector in a suitable microorganism.

17. The method of claim 15, wherein step (f) comprises PCR.

18. The method of claim 15, wherein said oligonucleotides are between 30 and 60 bases in length.

19. The method of claim 15, wherein step (g) comprises sequencing said fragment.

20. The method of claim 15, wherein step (d) comprises treating with sodium dodecyl sulfate or phenol/chloroform.

21. The method of claim 15, wherein said mammal is a human.

22. The method of claim 15, wherein said DNA polymerase is the exonuclease-deficient Klenow fragment of *E. coli* DNA polymerase I.

23. The method of claim 15, wherein said vector is a plasmid.

24. The method of claim 15, wherein said vector is a yeast artificial chromosome, bacterial artificial chromosome or P1 phage derived artificial chromosome.

25. The method of claim 15, further comprising the step of size fractionating said DNA fragments of step (a) to enrich for the fragment containing the mutation.

26. The method of claim 25, further comprising prior to the ligating step, ligating the enriched DNA fragments to a biotinylated duplex containing complementary cohesive ends, wherein said biotinylated duplex is bound to streptavidin-coated beads.

* * * * *

UNITED STATES PATENT AND TRADEMARK OFFICE
CERTIFICATE OF CORRECTION

PATENT NO. : 5,707,811
DATED : January 13, 1998
INVENTOR(S) : Ferrin et al.

Page 1 of 2

It is certified that error appears in the above-identified patent and that said Letters Patent is hereby corrected as shown below:

On the title page, item [56]:

line 16, after "DNA sequence", please replace "dtermination" with --determination--.
Page 2, lines 29-30, please delete "Taidi-Laskowski et al. (1988) *Nucleic Acids Research* 16:8157-8169".
Column 2, line 23, after "fragment", please replace "coning" with --containing--.
Column 3, line 9, after "includes", please replace "recA" with --RecA--.
Column 3, line 49, after "a", please replace "genomie" with --genomic--.
Column 4, line 8, after "the", please replace "oligonueleotides" with --oligonucleotides--.
Column 4, line 31, after "HinfI", please replace "HpaII" with --HpaII--.
Column 5, line 48, before "that", please replace "molecities" with --molecules--.
Column 5, line 51, after "type", please replace "Ils" with --IIs--.
Column 8, line 9, after "protein", please replace "2.6 µg" with --26 µg--.
Column 8, line 21, after "EcoRI and", please replace "BarnHi" with --BamHI--.
Column 8, line 58, after "reaction,", please replace "0.34 µg" with --3.4 µg--.
Column 9, line 7, before "in 0.1 cm", please replace "electropotation" with --electroporation--.

UNITED STATES PATENT AND TRADEMARK OFFICE
CERTIFICATE OF CORRECTION

PATENT NO. : 5,707,811
DATED : January 13, 1998
INVENTOR(S) : Ferrin et al.

It is certified that error appears in the above-identified patent and that said Letters Patent is hereby corrected as shown below:

Column 15, line 24, after "digesting DNA", please replace "coning" with --containing--.
    Column 15, line 36, after "fragment", please replace "coming" with --containing--.
    Column 15, line 44, before "enzyme", please replace "restfiction" with --restriction--.

Signed and Sealed this

First Day of September, 1998

Attest:

BRUCE LEHMAN

*Attesting Officer*

*Commissioner of Patents and Trademarks*